United States Patent [19]

Iwasaki et al.

[11] Patent Number: 4,668,634

[45] Date of Patent: May 26, 1987

[54] SYRINGE TONOMETRIC APPARATUS AND METHOD

[75] Inventors: Dean H. Iwasaki, Denver; Michael D. Iliff, Conifer, both of Colo.

[73] Assignee: Marquest Medical Products, Inc., Englewood, Colo.

[21] Appl. No.: 776,573

[22] Filed: Sep. 16, 1985

[51] Int. Cl.[4] ............................................. G01N 33/50
[52] U.S. Cl. ..................................... 436/68; 436/174; 422/68
[58] Field of Search ............... 422/50, 68, 99; 436/11, 436/68, 174

[56] References Cited

U.S. PATENT DOCUMENTS

| | | |
|---|---|---|
| 3,127,254 | 3/1964 | Astrup et al. . |
| 3,873,271 | 3/1975 | Young et al. ..................... 422/68 X |
| 3,874,850 | 4/1975 | Sorensen et al. ................. 436/68 X |
| 3,973,915 | 8/1976 | Raffaele et al. . |
| 4,251,483 | 2/1981 | Carroll . |
| 4,253,845 | 3/1981 | Smernoff . |
| 4,256,461 | 3/1981 | Wallace et al. . |
| 4,358,424 | 11/1982 | Weber et al. . |
| 4,567,748 | 2/1986 | Kloss ................................ 436/11 X |

OTHER PUBLICATIONS

Noonan et al., Clinical Chemistry, vol. 20, No. 6, 1974, pp. 660–665, "Quality-Control System for Blood pH and Gas Measurements, with Use of a Tonometered Bicarbonate-Chloride Solution and Duplicate Samples of Whole Blood".

Primary Examiner—Charles Hart
Attorney, Agent, or Firm—Sheridan, Ross & McIntosh

[57] ABSTRACT

Method and apparatus are provided to equilibrate a solution contained in a conventional syringe. The syringe is positioned so that the tapered end of the syringe is upward relative to the flanged end of the syringe. An equilibration tube member is inserted into the tapered end of the syringe. Equilibrating gas of a known composition is delivered to an input cavity formed in a heat block. The equilibrating gas is humidified in a humidifying chamber after it exits the input cavity. The humidified, equilibrating gas then passes into an output cavity formed in the heat block. The equilibration tube member receives the gas from the output cavity and carries it downwardly into the syringe where it exits the equilibration tube member into the equilibration solution. The equilibrating gas passes upwardly through the solution to produce an equilibrated sample. Gas passing from the solution is able to exit the syringe through its tapered end.

26 Claims, 6 Drawing Figures

SYRINGE TONOMETRIC APPARATUS AND METHOD

FIELD OF THE INVENTION

The present invention relates to tonometers and, in particular, to a tonometer in which the equilibrated sample is produced in a syringe.

BACKGROUND INFORMATION

In conjunction with analyzing the blood gas content of arterial blood, it is necessary that a high degree of quality control be maintained in connection with the operation of the blood gas analyzer. A common approach for determining and monitoring the accuracy and precision of a blood gas analyzer is to utilize a control or standard sample of known composition. The control sample is inputted to the blood gas analyzer and analyzed to check whether the resulting output corresponds to the expected output. If the comparison does not indicate a correspondence, the blood gas analyzer may be calibrated to insure correspondence and proper operation of the analyzer.

To produce the control sample, a number of different tonometric apparatuses have been developed. In particular, a number of tonometers have been advanced for equilibrating a gas and liquid in a chamber for producing a control sample. In one class of tonometers, control samples are produced in modified syringes. In one of such syringetype tonometers, the tip of the syringe is inverted, or located downwardly relative to the opened end of the syringe barrel, and placed into a temperature-controlled chamber while the plunger of the syringe extends in the opposite direction away from the chamber. The equilibrating gas is inputted into the syringe tip through a valve. A venting hole is formed in the syringe barrel at the opposite end of the tip. Gas moves from the tip of the syringe to the opposite end of the syringe barrel and gas is able to exit the venting hole. In another syringe-type tonometer, the syringe is not inverted but, instead of entering the syringe tip, the equilibrating gas flows in the direction from the bottom of the syringe barrel to the syringe tip. This tonometer also includes a humidifying chamber in the syringe itself. In another group of tonometers, chambers or containers are utilized in preparing the equilibrated solutions and such solutions are removed from the chamber after the control sample has been made. With regard to such tonometers, it is common to use a conventional syringe, but only for removal of the control sample from the chamber, and not as a chamber in which an equilibrated solution is produced.

Each of these tonometers suffers from one or more drawbacks that reduce its effectiveness and operability thereby minimizing meaningful acceptance of the tonometer by potential users. In the case of previously devised syringe tonometers, a conventional syringe must be modified in order to provide required features associated with the tonometer operation. For example, a venting hole must be provided at the bottom end of the syringe in one case and, in the other, a syringe must be provided that is able to provide a humidifying chamber and house a pair of membranes. Additionally, problems can occur relating to valve leakage while the valve is attached to the syringe tip. And, in the case of equilibrating blood housed in the syringe, when it is necessary to remove air trapped in the syringe, the vent hole must be covered and the user may contact the blood to provide the covering. With regard to non-syringe tonometers, it is always necessary to remove the equilibrated solution from the chamber in which it was made so that it can be transported and inputted to the blood gas analyzer whereby diminution of the quality of the sample can occur during such a transfer of the sample.

SUMMRY OF THE INVENTION

The present invention is directed to a tonometer which includes a syringe for use in preparing a control sample that is to be inputted to a blood gas analyzer. The syringe is positioned so that the tapered portion or tip of the syringe is positioned upwardly relative to the bottom of the syringe barrel. The syringe need not be modified in order to prepare the control sample and the sample need not be transferred to a conveying and/or inputting device for transfer to the blood gas analyzer.

More particularly, the tonometer includes a housing that contains a heat block supported within the housing. The heat block includes a number of channels formed in the front of the block. Each of the channels is formed of a size to receive a conventional syringe. The conventional syringe includes a syringe barrel having a tapered end to which a needle can be attached and a flanged end opposite the tapered end. The syringe includes a plunger that is inserted through the flanged end. The plunger includes a rod and a sealing plug connected to the rod. A support block is mounted on top of the heat block. A number of equilibration tubes are connected to the support block with the number of equilibration tubes corresponding to the number of channels formed in the heat block. Each conventional syringe is mounted in one of the channels such that the tapered end of the syringe is located upwardly relative to the flanged end of the syringe barrel. Each equilibration tube is movable to be received through the tapered end and into the syringe barrel with the length of the equilibration tube being such that it terminates above the face of the sealing plug. The syringe is supported in the heat block using a pair of spaced rails which receive and support portions of the flanged end of the syringe barrel.

For each channel and syringe, a pair of cavities are formed in the body of the heat block. Each of the two cavities extends from the top of the heat block to its bottom. One of the two cavities is an input cavity for receiving gas to be humidified while the second of the two cavities is an output cavity which receives the humidified gas. A heat exchanging element is inserted and held in each of the output cavities to maximize the efficiency of the heat exchange between the passing humidified gas and the heat block. Each of the humidifying chambers that communicate with corresponding input and output cavities includes a cylindrical-shaped vial that is preferably transparent. An inner sealing ring and an outer sealing ring are connected to the top portion of each of the humidifying chambers. The inner sealing ring surrounds an aperture that provides communication between the input cavity and the interior of the chamber. The outer sealing ring surrounds an aperture that provides communication between the output cavity and the chamber. Each humidifying chamber is also supported by the spaced rails at its top portion with the humidifying chamber being located rearwardly of the syringe, but preferably, being spaced downwardly from the heat block so that it can be seen.

In operation, the present invention is able to provide a number of control or standard samples for use with a blood gas analyzer. In connection with the production of a control sample in one of the syringes, equilibrating gas is fed into the back of the housing and directed through tubing to one of the input cavities formed in the heat block. The gas is heated by passing through the input cavity and exits the humidifying tube into the humidifying chamber that communicates with the input cavity. The humidifying chamber contains a humidifying liquid, such as distilled water. Gas bubbles up from the distilled water and enters the output cavity formed in the heat block. The desired temperature of the gas is maintained while passing through this output cavity and while contacting the heat exchanging element. The upward moving heated gas then passes into the equilibration tube which is inserted through the tapered end of the conventional syringe. The heated and humidified gas exits the bottom end of the equilibration tube typically adjacent to the sealing plug of the syringe. The gas then travels upwardly into the equilibration solution provided in the conventional syringe. A vent for gas is provided by the tapered end of the syringe. When it is determined that a proper equilibrated sample has been produced using the equilibration sample and the inputted gas, the syringe is removed from the equilibrating tube and the heat block for transport to the blood gas analyzer. The equilibrated sample is inputted to the blood gas analyzer by injecting the sample from the syringe using the syringe plunger.

Based on the foregoing summary, a number of worthwhile objectives of the present invention become evident. A tonometer is provided that utilizes a conventional syringe that need not be modified. As a result, conventional, relatively inexpensive parts can be incorporated into the present invention and the labor associated with making such parts is reduced. For example, a venting hole need not be formed in the conventional syringe since the tapered end is able to provide the desired venting function. The present invention also enables the user to make a number of equilibrated samples at one time because a number of conventional syringes can be filled with equilibration solution and mounted in separate channels formed in the heat block. Additionally, in one embodiment, the humidifying chamber is transparent and located away from the heat block so that the operator is able to watch the bubbling gas as it enters the humidifying liquid. This visual inspection enables the operator to determine that there is sufficient gas flow to prepare a control sample for eventual use in the blood gas analyzer. The design of the heat block of the present invention also facilitates the insertion and removal of the humidifying chambers and syringes while providing a compact configuration.

Additional advantages of the present invention will become readily apparent from the following discussion, when taken in conjunction with the accompanying drawings.

DETAILED DESCRIPTION OF THE PREFERRED EMBODIMENTS

Figure 1:
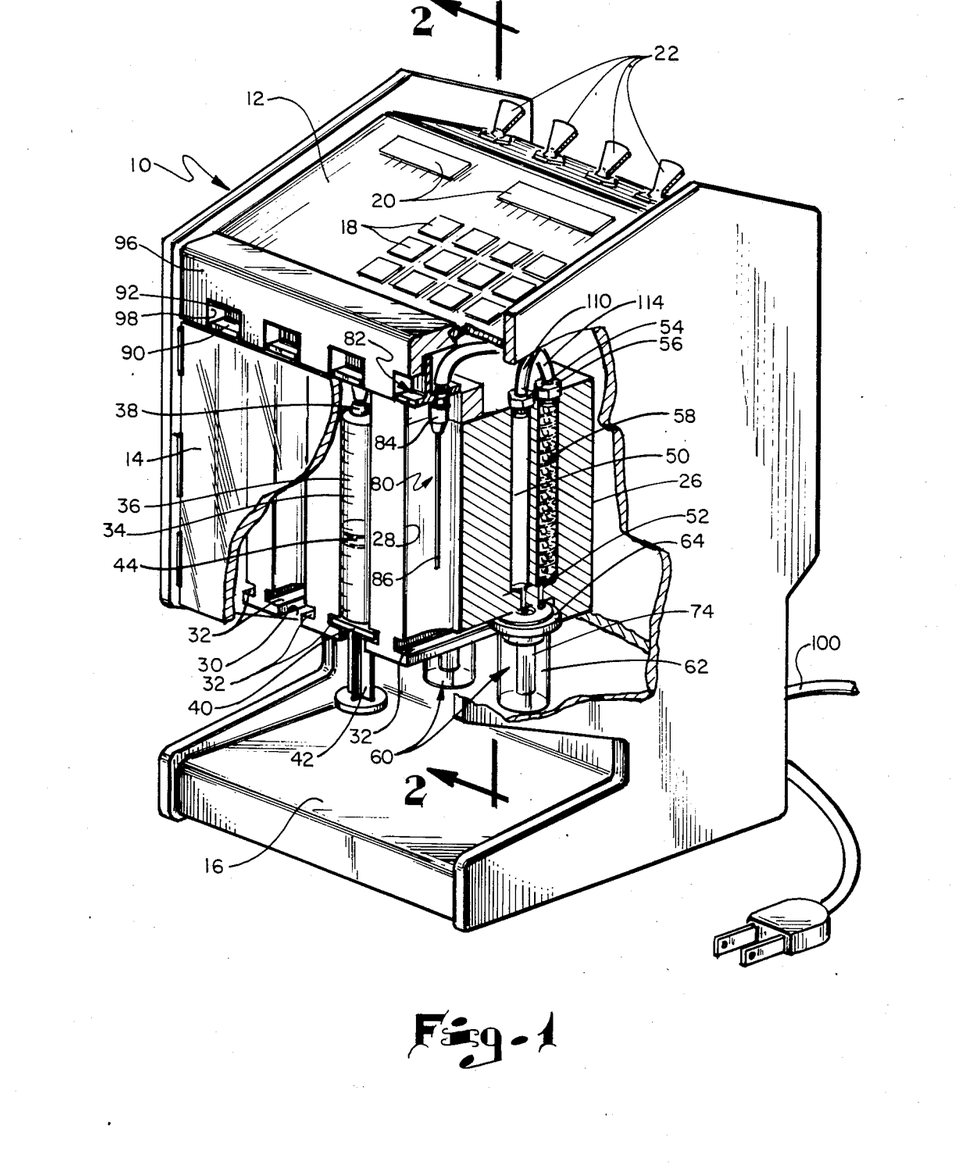
FIG. 1 is a perspective view of the tonometer of the present invention with a portion of the housing and heat block being cut away to better illustrate the syringe mounted in the heat block and the input and output cavities.

In accordance with the present invention, a tonometric apparatus is disclosed which utilizes a conventional, unmodified syringe as the equilibration chamber. Referring first to FIG. 1, the apparatus includes a housing 10. The housing 10 includes a top panel 12, a front door 14, and a platform 16 spaced from the front door 14. The front door 14 is conventionally attached to the remaining portions of the housing 10 using a hinge and also includes a latch for holding the front door 14 closed. In the embodiment shown in FIG. 1, the top panel 12 is illustrated as having a number of operating/control switches 18 and indicators 20 which can be used in operating the tonometric apparatus. The operating/control switches 18 and the indicators 20 communicate with electronic hardware for use in monitoring time, among other functions. By way of example, an amount of time is inputted by the operator using the operating/control switches 18. The amount of time is used in determining whether the equilibrating gas is flowing at a desired rate and when the equilibration process is completed, as will be discussed in greater detail later. Also mounted on the top panel 12 are a number of toggle valves 22 for use in controlling the flow of gas through the tonometer.

Figure 3:
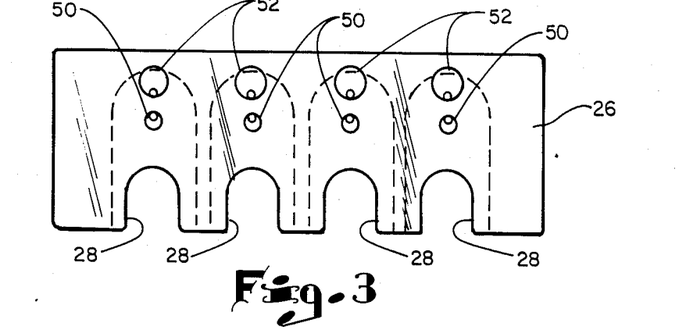
FIG. 3 is a top plan view of the heat block showing the top of the input and output cavities and the top portions of the channels formed in the heat block.
Figure 4:
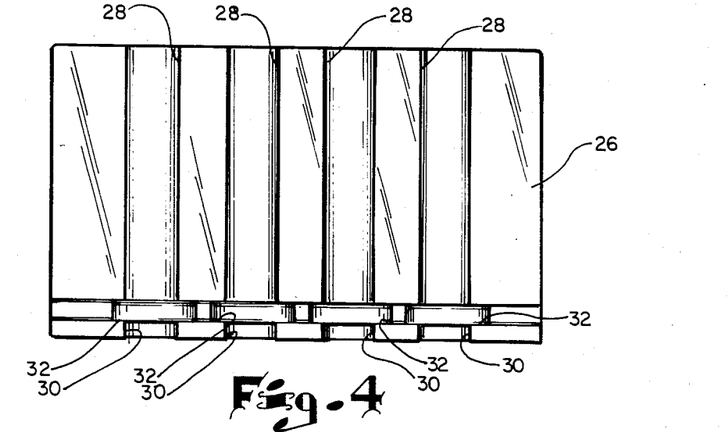
FIG. 4 is a front elevational view of the heat block showing the longitudinally extending channels and the rails formed in the bottom of the heat block for receiving the flanged ends of the syringes and the top portion of the humidifying chambers.
Figure 5:
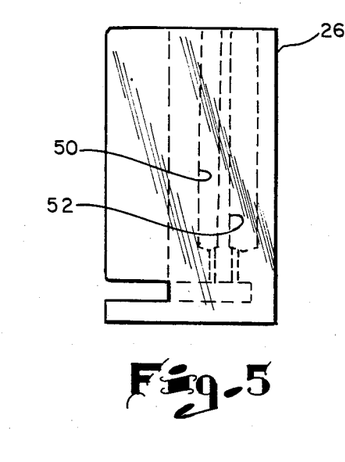
FIG. 5 is a side elevational view of the heat block.

With reference to FIGS. 3–5 also, mounted within the housing 10 is a heat block 26 having a number of longitudinally extending channels 28 formed in a front side of the heat block 26. The heat block may be made of metal, another homogeneous solid, or of a suitable laminated material. The heat block 26 is connected to a source of heat so that the heat block 26 can be maintained at a desired temperature. For each channel 28, laterally extending cut-outs 30 are integrally formed to define a pair of spaced rails 32 which extend from the front of the heat block 26 to its back. In another embodiment, the rail support structure is formed separately and connected to the heat block by conventional fasteners. Each of the channels 28 is of a size for receiving a conventional syringe 34. The syringe includes a syringe barrel 36, a tapered end 38, a flanged end 40 and a plunger rod 42 with a sealing plug 44 attached to the end of the plunger rod 42. Each channel 26 is able to receive the syringe barrel 36 while the flanged end 40 is inserted into and held by the rails 32. In the embodiments shown, four channels 28 are provided for use in producing four equilibrated or control samples.

Figure 2:
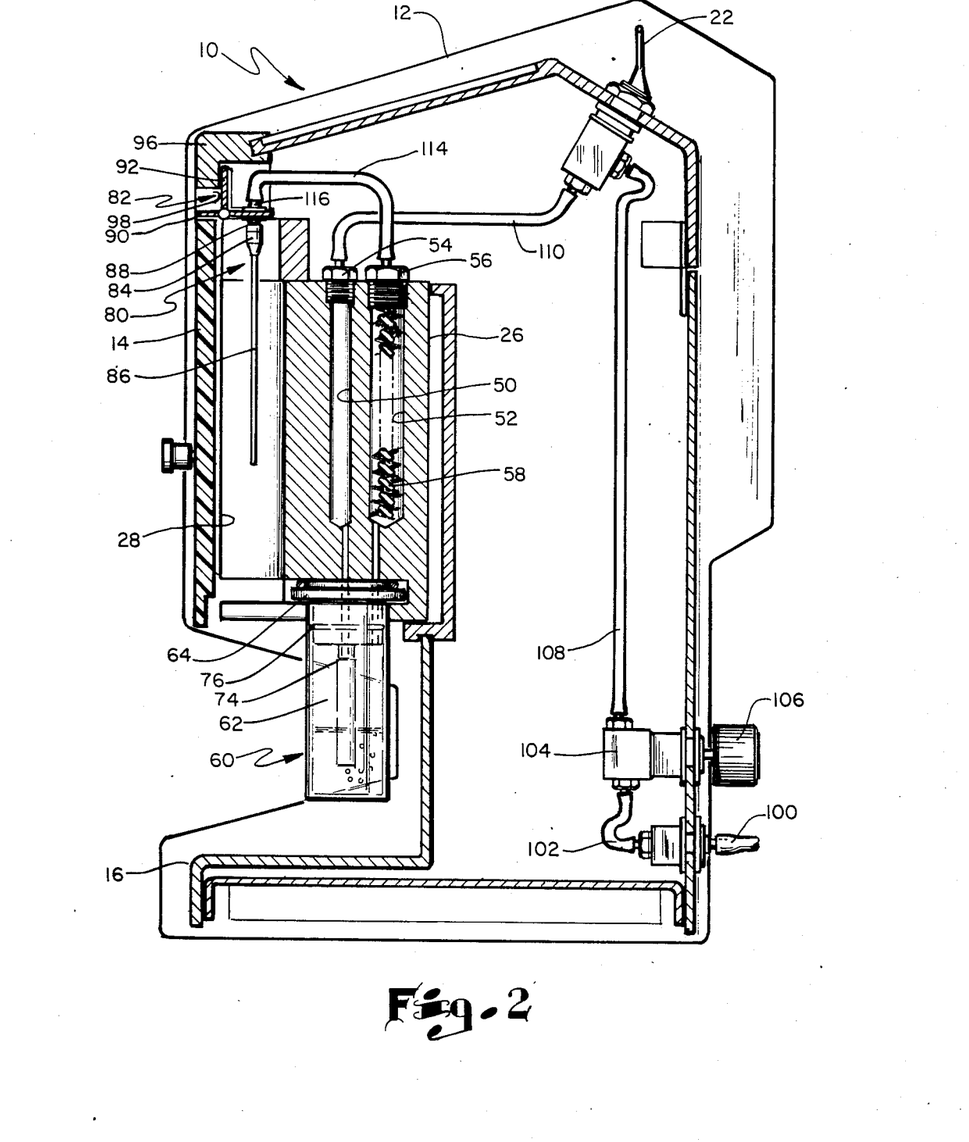
FIG. 2 is a side elevational view illustrating the elements used to carry the equilibrating gas through the tonometer to the equilibration tube.

The heat block 26 is also formed with a number of cavities through which equilibrating gas passes. For each channel 28, an inlet cavity 50 and an output cavity 52 are formed. In the embodiment shown, each inlet cavity 50 is located more adjacent to its corresponding channel 28 than is the output cavity 52. As also can be seen, the inlet cavity 50 has a smaller diameter than the output cavity 52. As illustrated in FIGS. 1 and 2, a conventional fitting 54 is attached to the top of the input cavity 50 and a conventional fitting 56 is attached to the top of the output cavity 52. Each input cavity 50 extends vertically through the heat block 26, as seen in FIGS. 1 and 2. Each input cavity 50 terminates in a decreased diameter at the bottom end of the heat block 26. Each output cavity 52 extends vertically through the heat block 26 and also terminates in a decreased diameter at the bottom end of the heat block 26. In one embodiment, each output cavity 52 receives and contains a heat exchanger 58 in the form of a bristle brush. The heat exchanger 58 acts to increase the surface area contacted by the gas during its passage through the output cavity 52 to better maintain the gas at a desired temperature. It is also contemplated by the present invention that each of the input cavities 50 could also contain a heat exchanger. In another alternative, only the input cavities and not the output cavities would contain a heat exchanger.

Figure 6:
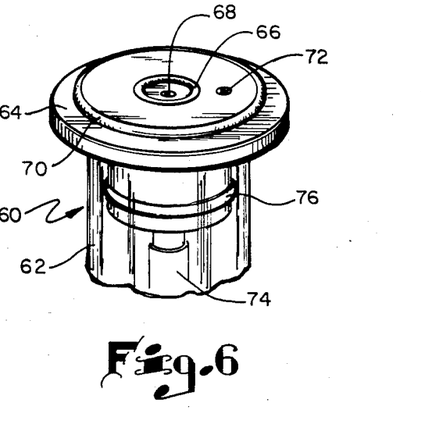
FIG. 6 is a top plan view of the humidifying chamber illustrating the inner and outer sealing rings with apertures provided within the sealing rings.

The tonometric apparatus further includes a number of humidifying assemblies 60, with the number of such humidifying assemblies 60 corresponding to the number of channels 28, as well as syringes 34. Each humidifying assembly 60 is supported using a pair of the spaced rails 32. The humidifying assembly 60 is located inwardly relative to its corresponding syringe 34 and adjacent to the back of the heat block 26. Each humidifying chamber 60 communicates with corresponding input and output cavities 50, 52. Referring also to FIG. 6, each humidifying assembly 60 includes a humidifying chamber 62 with a cap or top portion 64 covering the top of the chamber 62. Positioned on the cover is an inner sealing ring 66 with an inner aperture 68 formed through the cap 64 but surrounded by the inner sealing ring 66. Also provided on the cap 64 is an outer sealing ring 70, which is concentric with and spaced outwardly from the inner sealing ring 66. An outer aperture 72 is provided through the cap 64 and is located between the inner sealing ring 66 and the outer sealing ring 70. Each humidifying assembly 60 also includes a humidifier tube 74 that communicates with the inner aperture 68 and the input cavity 50 communicating with the particular inner aperture 68. The humidifier tube 74 extends from the cap 64 down into the humidifying chamber with the end of the humidifier tube 74 terminating a desired distance from the bottom of the humidifying chamber 62. A sealing O-ring 76 is also provided and is connected to the cap 64 to form a seal between the cap 64 and the inner surface of the chamber 62. In the preferred embodiment, the humidifying chamber 62 is transparent so that the gas bubbles formed in the humidifying chamber 62 due to the inputted gas can be seen by the operator. In another embodiment, the length of the heat block 26 is extended so that at least most of each humidifying assembly 60 is surrounded by the heat block 26. In such a case, the temperature of the inputted gas can be maintained at a desired temperature with greater certainty since the heat block 26 is used to heat the gas even while it is being humidified in the humidifying assembly 60.

The tonometer also includes a number of equilibration tube members 80, as seen in FIGS. 1 and 2, each of which is connected to a lever assembly 82. In the embodiment shown, each equilibration tube member 80 includes a needle hub 84 and a cannula 86. Each needle hub 84 is connected to a male Luer taper 88 of the lever assembly 82. Both the number of equilibration tube members 80 and the number of lever assemblies 82 correspond to the number of channels 28, as well as syringes 34, that can be used at any one time to equilibrate samples. Each lever assembly 82 includes a lateral arm 90 and a vertical arm 92 connected to the lateral arm 90. The arms 90, 92 are pivotal about a laterally-extending pivot pin (not shown) to permit movement of the equilibration tube member 80 towards the front of the tonometer after the door 14 is opened.

Each of the lever assemblies 82 is connected to a support block 96. The support block 96 is formed with a number of vertically-extending slots 98. In order that each of the cannulas 86 be readily positioned within a syringe 34 received in a channel 28 adjacent to the equilibration tube member 80, the lever assembly 82 is located within the slot 98. Each equilibration tube member 80 is substantially rigid and extends downwardly from the support block 96 for a desired distance. Each lever assembly 82 can be pivoted to move the equilibration tube member 80 connected thereto so that the tapered end 38 of a syringe 34 can readily receive the cannula 86. In another embodiment, instead of the lever assembly 82 as shown, a rotatable wheel can be used in pivoting the equilibration tube member 80. Additionally, it is not necessary that a relatively rigid equilibration tube member 80 be used. A flexible tube can also be used for placement by the operator into the barrel 36 of the syringe 34.

In connection with the delivery of the equilibrating gas and with reference in particular to FIG. 2, the apparatus further includes a number of gas inlet tubes 100 located at the back of the housing 10. The number of gas inlet tubes 100 equals the number of syringes 34 that can be used with the tonometer at one time. Each gas inlet tube 100 is connected to an inlet tubing 102 located within the housing 10. The inlet tubing 102 is connected to a needle valve 104. The opening of the valve 104 is regulated by a valve control member or knob 106, which is accessible by the operator for regulating the flow of gas out of the valve 104. The valve 104 acts to control the amount of gas inputted into the tonometric apparatus. Connected to the output of the needle valve 104 is a first intermediate tube 108. Like the gas inlet tube 100, the number of inlet tubing 102 pieces, needle valves 104, valve control members 106, and first intermediate tubes 108 equals the number of syringes 34 that can be used with the tonometer at one time. Each first intermediate tube 108 extends to one of the four toggle valves 22 located on the top panel 12. The output side of each toggle valve 22 communicates with a second intermediate tube 110. The second intermediate tubes 110 connect the output of the toggle valves 22 to a corresponding one of the input cavities 50 using one of the fittings 54. To carry the humidified and heated gas from the heat block 26, an outlet tubing 114 is provided and connected to one of the fittings 56. The other end of the outlet tubing 114 is connected to a conventional fitting 116 adjacent to a syringe 34.

In order to produce an equilibrated sample, a number of steps are required. Inasmuch as the same steps are performed in connection with each equilibration sample made in one of the syringes 34, it is only necessary to describe the operation for one syringe 34, keeping in mind that the described process applies to each equilibrated sample made in the other of the syringes 34.

Initially, the humidifying chamber 62 is filled to a desired level with a humidifying liquid, such as distilled water. The cap 64 is used to cover the top of the humidifying chamber 62. The humidifying assembly 60 is then slid along the rails 32 until it contacts the back of the heat block 26. In this position, the inner aperture 68 communicates with the input cavity 50 while the outer aperture 72 communicates with the output cavity 52. The inner sealing ring 66 provides a seal between the two apertures 68, 72 while the outer sealing ring 70 provides a seal between the environment and the inner sealing ring 66. Because of this configured humidifying assembly 60, the cap 64 need not be specially positioned relative to the input and output cavities 50, 52. Regardless of where the outlet aperture 72 is located relative to the bottom end of the output cavity 52, the gas can only escape from the outlet aperture 72 into the output cavity 52 because of the presence of the two sealing rings 66, 70.

In addition to filling the humidifying chamber 62 by the foregoing method, it can also be filled after the humidifying assembly 60 is connected to the heat block 26. Specifically, because of a friction fit or connection between the humidifying chamber 62 and the cap 64 using the O-ring 76, the humidifying chamber 62 can be separated from the cap 64 by pulling downwardly away from the cap 64 to overcome the friction connection. After the humidifying chamber 62 is filled to a desired level, the humidifying chamber 62 can be re-connected to the cap 64. This particular configuration for the humidifying assembly 60 also enables the humidifying assembly to act as a safety device. That is, when the pressure in the humidifying chamber 62 exceeds a predetermined magnitude, the pressure causes the humidifying chamber 62 to disengage or pop-off from the cap 64 to provide an outlet in order to relieve the unwanted pressure. Relatedly, because the humidifying chamber 62 is disconnected, there is no backflow of liquid through the tonometer and, consequently, no liquid will be carried into gas passageways. As a result, there is no contamination of such passageways by the liquid.

After the humidifying assembly 60 is properly located beneath the cavities 50, 52, the conventional syringe 34 can be placed in the corresponding channel 28. The syringe 34 is first filled to a desired level with equilibration solution, with the desired level being achieved by movement of the plunger 42 and sealing plug 44 away from the tapered end 38 of the syringe 34 to define a preset volume in the syringe barrel 36. The syringe 34 containing the equilibration solution is then mounted in the channel 28 of the heat block 26. This is accomplished by positioning the equilibration tube member 80 somewhat outwardly from the channel 28 so that the operator is able to insert the cannula 86 into the syringe barrel 36 through the tapered end 38. With the cannula 86 inside the syringe 34, the syringe barrel 36 can be placed in the channel 28 such that the flanged end 40 is supported on the spaced rails 32 located at the bottom of the channel 28. When in position, the tapered end 38 extends part way into the slot 98 formed in the support block 96. As can be appreciated, the cannula 86 should have a length less than the distance between the top of the syringe 34 and the top of the sealing plug 44 of the syringe 34.

Before supplying the equilibrating gas to the tonometer, the heat block 26 should be at the desired, predetermined temperature. The temperature of the heat block 26 can be controlled using electronic hardware including a thermistor. In one embodiment, the temperature of the heat block should be about 37° C. before delivering the equilibrating gas into the tonometer. After the desired temperature is reached and with the pre-filled syringe 34 and humidifying assembly 60 in place, the toggle valve 22 is opened. The valve control member 106 can be used by the operator to adjust or throttle the flow rate of gas through the needle valve 104. The toggle valve 22 receives the equilibrating gas from the first intermediate tube 108.

From the toggle valve 22 the equilibrating gas passes to the second intermediate tube 110. From the tube 110, the gas enters input cavity 50. At the bottom of the heat block 26, the equilibrating gas passes from the input cavity 50 into the inlet aperture 68 formed in the cap 64. From the inlet aperture 68, the gas enters the humidifier tube 74. The free end of the humidifier tube 74 extends into the humidifying liquid so that the gas exits the humidifier tube 74 into the humidifying liquid and bubbles upwardly through the humidifying liquid. The humidified gas is able to escape through the outer aperture 72 formed in the cap 64. Since the outer aperture 72 communicates with the output cavity 52, the gas enters the bottom end of the heat block 26 and passes into the output cavity 52 where it contacts the bristle brush heat exchanger 58. The humidified equilibrating gas is maintained at the desired temperature using the heat exchanger 58 and then passes through the output port 52 into the outlet tubing 114.

From the outlet tubing 114, the gas enters the fitting 116 which communicates with the male Luer taper 88 connected to the equilibration tube member 80. The gas passes down the equilibration tube member 80 and exits the free end of the cannula 86 at a position within the equilibration solution. Upon exiting, the gas mixes with the equilibration solution for use in providing an equilibrated sample. Gas that escapes the equilibration solution passes from the top of the syringe barrel 36 and out the tapered end 38 of the syringe 34.

In connection with producing a control sample for use in a blood gas analyzer, the operator may use the electronic timer provided with the tonometer of the present invention. For example, the timer can be used in providing two functions. First, to ensure that there is a desired equilibrating gas flow rate, the timer is used in determining the gas flow rate. In particular, the operator waits until bubbles are seen exiting the humidifier tube 74, which preferably has a relatively large exit end so that the gas bubbles can be readily viewed as they exit the humidifier tube 74. The timer is preset to a desired time within which the gas bubbles are to be counted. After the gas bubbles begin exiting the humidifier tube 74, the timer is activated and at the same time bubbles exiting the humidifier tube are counted by the operator. When the preset time has elapsed, the timer provides an indication that the time has expired and the operator can then determine whether the number of bubbles counted during the preset time is within a predetermined and desired range of time. If such is the case, the gas flow rate is proper.

Secondly, the electronic timer can be used in determining the end of production of a control sample. Specifically, after the proper gas flow rate is obtained, a predetermined time is set in the timer by the operator. The timer is started and at the end of the predetermined time, an indication is given. From this indication, the operator is informed that a control sample has been produced and, if desired, can be inputted to a blood gas analyzer. The time required to produce a fully equilibrated sample depends upon a number of factors including the flow rate of the equilibrating gas, the temperature of the heat block 26, and the amount of equilibration solution present in the syringe 34. By way of example, for a flow rate of 1.5-4 gas bubbles/second being generated in the humidifying chamber 62, a heat block temperature of 37° C., and three cubic centimeters of equilibration solution, the sample is fully equilibrated in the syringe 34 in about thirty minutes.

The present invention also contemplates the elimination of foaming due to extensive bubble production in the syringe 34 during the tonometric process. To overcome such a problem, the equilibration solution may include an anti-foaming agent or, alternatively, a small device may be provided in the syringe for use in breaking up gas bubbles.

After the sample in the syringe 34 is fully equilibrated and the equilibrating gas to the humidifying assembly 60 is shut off, the syringe 34 is removed from the channel 28. Specifically, the bottom of the syringe barrel 38 is moved outwardly from the channel 28 causing the equilibration tube 80 to pivot outwardly. Once the flanged end 40 of the syringe 34 is no longer supported by the rails 32, the syringe 34 can be pulled away from the equilibration tube 80. After removal, the operator is able to remove any air that might be present at the top of the syringe 34 by moving the plunger rod 42 forwardly into the barrel 36. With any excess air removed, the tapered end 38 can be covered and the equilibration sample can be later used in quality control of the blood gas analyzer. In a case in which the equilibrated sample is to be inputted immediately to a blood gas analyzer, the tapered end 38 is not covered but is inserted into an appropriate input port provided with the blood gas analyzer. The plunger rod 42 is then moved forward into the barrel 36 causing the equilibrated sample to exit the tapered end 38 and enter the blood gas analyzer. With the equilibrated sample of known gas constituents ready for analysis, the blood gas analyzer is activated and a determination made as to whether the output of the blood gas analyzer corresponds to the known gas constituents.

Based on the foregoing detailed description of the invention, a number of advantages are readily seen. A tonometer is provided that utilizes a conventional syringe as an equilibrating chamber. As a consequence, new and unconventional parts need not be fabricated for the equilibration chamber. Furthermore, the conventional syringe can be used to transfer the equilibrated sample to the blood gas analyzer without messy and complicated transfers of the equilibration sample. Because the tapered end of the syringe is located upwardly relative to the flanged end, an equilibrating tube is provided so that humidified, equilibrating gas passes downwardly into the syringe barrel and then upwardly where gas is able to escape the tapered end. In this configuration, the tapered end acts as a vent and the conventional syringe need not be modified to provide a gas vent. Because a conventional syringe is utilized, the humidifying chamber is provided separately from the equilibration chamber and is uniquely configured to facilitate the entry and exit of equilibrating gas. In addition, in the preferred embodiment, a heat exchanger is utilized in the output cavity to maintain the equilibrating gas at a desired temperature. And, the humidifying liquid is not surrounded by the heat block so that the operator is able to see and count the number of gas bubbles being generated in the humidifying chamber.

Although the present invention has been described with reference to certain embodiments, it should be readily appreciated that further variations and modifications can be effected within the spirit and scope of this invention.

What is claimed is:

1. A method for producing an equilibrated sample, comprising:
   providing a syringe having a barrel, a plunger rod, a sealing plug connected to said plunger rod, and a tapered end;
   placing solution to be equilibrated into said syringe;
   positioning said tapered end of said syringe upwardly relative to said plunger rod;
   providing humidifying means;
   placing gas delivery means into said tapered end of said syringe;
   delivering gas to said humidifying means;
   humidifying gas using said humidifying means;
   sending gas to said gas delivery means;
   allowing gas to pass downwardly using said gas delivery means into said syringe barrel; and
   allowing gas to pass upwardly through said solution to provide an equilibrated sample in said syringe.

2. A method, as claimed in claim 1, further including:
   allowing at least a portion of said gas to escape from said tapered end of said syringe.

3. A method, as claimed in claim 1, further including:
   keeping said humidifying means separate from said syringe.

4. A method, as claimed in claim 1, further including:
   providing said syringe with a flanged end and supporting said syringe using said flanged end.

5. A method, as claimed in claim 1, further including:
   controlling the flow of gas using two separate control means.

6. A method, as claimed in claim 1, wherein:
   said providing of said humidifying means includes positioning said humidifying means for viewing of gas bubbles being formed in said humidifying means.

7. A method, as claimed in claim 1, wherein:
   said placing of said gas delivery means includes providing an equilibration tube and pivoting said equilibration tube for insertion into said tapered end of said syringe.

8. A method, as claimed in claim 1, wherein:
   said sending of said gas to said gas delivery means includes contacting said gas with a heat exchanger.

9. A method, as claimed in claim 1, wherein:
   said providing of said syringe includes presetting said sealing plug in said syringe barrel to a desired position, said position being adjustable and depending upon the amount of said solution to be placed in said syringe.

10. A method, as claimed in claim 1, wherein:
    said providing of said humidifying means includes providing a humidifying chamber and a cap, connecting said humidifying chamber and said cap by friction, and disconnecting said humidifying chamber from said cap when a predetermined pressure is exceeded in said humidifying chamber.

11. A method, as claimed in claim 1, further including:
    timing the number of gas bubbles for a predetermined time using digital circuitry.

12. A method, as claimed in claim 1, further including:
    timing the production of the equilibrated sample for a predetermined time using digital circuitry.

13. An apparatus for providing an equilibrated sample, comprising:
a syringe having a barrel, a plunger rod, a sealing plug connected to said plunger rod, and a tapered end, a solution to be equilibrated being held in said syringe barrel;
heating means having at least one channel formed therein, said syringe being positioned in said channel wherein said tapered end of said syringe is located upwardly relative to said plunger rod, said heating means including a body having an input cavity formed therein and an output cavity formed therein but spaced from said input cavity and also including heat exchanging means located in at least one of said input cavity and said output cavity;
humidifying means containing a liquid for humidifying an equilibrating gas; and
gas delivery means in operative association with said syringe, said gas delivery means for providing gas into said solution and wherein said gas moves upwardly and then downwardly relative to said syringe barrel.

14. An apparatus, as claimed in claim 13, wherein:
said heating means includes support means provided at an end of said heating means for use in supporting said syringe and said humidifying means.

15. An apparatus, as claimed in claim 14, wherein:
said support means includes a pair of spaced, laterally-extending rails.

16. An apparatus, as claimed in claim 13, wherein:
said humidifying means is spaced from and out of alignment with said syringe.

17. An apparatus, as claimed in claim 13, wherein said humidifying means includes:
a humidifying chamber;
a cap having an inlet aperture and an outlet aperture;
first sealing means surrounding said inlet aperture; and
second sealing means surrounding said outlet aperture.

18. An apparatus, as claimed in claim 13, wherein said gas delivery means includes:
gas regulating means for regulating the flow rate of said gas provided to the apparatus; and
gas passage means communicating with said gas regulating means for preventing the flow of gas to said heating means, said gas passage means being separate from said gas regulating means.

19. An apparatus, as claimed in claim 13, further including:
timing means for use in monitoring time in determining whether the solution in said syringe is properly equilibrated.

20. An apparatus for providing an equilibrated sample, comprising:
a syringe having a barrel, a plunger rod, a sealing plug connected to said plunger rod, and a tapered end, a solution to be equilibrated being held in said syringe barrel;
heating means having at least one channel formed therein, said syringe being positioned in said channel wherein said tapered end of said syringe is located upwardly relative to said plunger rod;
humidifying means containing a liquid for humidifying an equilibrating gas; and
gas delivery means in operative association with said syringe, said gas delivery means for providing gas into said solution and wherein said gas moves downwardly and then upwardly relative to said syringe barrel, said gas delivery means including an equilibration tube member connected above said channel, at least a portion of said equilibration tube member extending downwardly into said syringe.

21. An apparatus for providing an equilibrated sample, comprising:
a syringe having a barrel, a plunger rod, a sealing plug connected to said plunger rod, and a tapered end, a solution to be equilibrated being held in said syringe barrel, said syringe being an unmodified, conventional syringe;
heating means having at least one channel formed therein, said syringe being positioned in said channel wherein said tapered end of said syringe is located upwardly relative to said plunger rod;
humidifying means containing a liquid for humidifying an equilibrating gas; and
gas delivery means in operative association with said syringe, said gas delivery means for providing gas into said solution and wherein said gas moves downwardly and then upwardly relative to said syringe barrel.

22. An apparatus for providing an equilibrated sample, comprising:
a syringe having a barrel, a plunger rod, a sealing plug connected to said plunger rod, and a tapered end, a solution to be equilibrated being held in said syringe barrel;
heating means having at least one channel formed therein, said syringe being positioned in said channel wherein said tapered end of said syringe is located upwardly relative to said plunger rod;
humidifying means containing a liquid for humidifying an equilibrating gas, aaid humidifying means including a humidifying chamber and a cap, said humidifying chamber and said cap being connected together using friction so that said humidifying chamber and said cap being disconnected when a predetermined pressure is exceeded in said humidifying chamber; and
gas delivery means in operative association with said syringe, said gas delivery means for providing gas into said solution and wherein said gas moves downwardly and then upwardly relative to said syringe barrel.

23. An apparatus for providing an equilibrated sample, comprising:
a plurality of means for containing equilibrated samples;
heating means including a body and having a number of channels formed in a side of said body, said body also having a plurality of input cavities and output cavities, each of said channels being associated with a corresponding one of said input cavities and a corresponding one of said output cavities;
a plurality of humidifying means, at least a first of said humidifying means being connected to said heating means at an end of said heating means, said connection being located away from said channels, each of said humidifying means including a chamber and a cap, an inlet aperture formed in said cap and communicating with said input cavity and an outlet aperture being formed in said cap and communicating with said output cavity; and
gas delivery means communicating with said heating means and said first humidifying means for carrying gas, said gas delivery means including a tube located in one of said means for containing for passing gas downwardly.

24. An apparatus, as claimed in claim 23, wherein:
said plurality of means for containing includes at least one syringe having a barrel, a plunger rod, a sealing plug and a tapered end.

25. An apparatus for use in providing an equilibrated sample which can be used with one or more containers that are removable from the apparatus, comprising:
at least a first removable container for housing an equilibrated sample;
heating menas including a body and having at least a first channel formed in a portion of said body, said body also having a first cavity, said first channel being associated with said first cavity, said heating means including heat exchanging means located in said cavity;
humidifying means containing a liquid for use in humidifying an equilibrating gas and being adjacent to said heating means; and
gas delivery means operatively associated with said humidifying means for use in carrying gas.

26. An apparatus for use in providing an equilibrated sample which can be used with one or more containers that are removable from the apparatus, comprising:
at least a first container for housing an equilibrated sample;
heating means including a body and having at least a first channel;
humidifying means being adjacent to said heating means and containing a liquid for humidifying an equilibrating gas, said humidifying means including a humidifying chamber and a cap, said humidifying chamber and said cap being connected together using friction so that said humidifying chamber and said cap can be disconnected when a predetermined pressure is exceeded in said humidifying chamber; and
gas delivery means operatively associated with said humidifying means for use in providing gas.

* * * * *